(12) United States Patent
Itoh et al.

(10) Patent No.: US 7,111,500 B2
(45) Date of Patent: Sep. 26, 2006

(54) ANALYSIS METHOD USING PIEZOELECTRIC RESONATOR

(75) Inventors: Atsushi Itoh, Kanagawa (JP); Motoko Ichihashi, Kanagawa (JP)

(73) Assignee: ULVAC Inc., Chigasaki (JP)

( * ) Notice: Subject to any disclaimer, the term of this patent is extended or adjusted under 35 U.S.C. 154(b) by 166 days.

(21) Appl. No.: 10/739,397

(22) Filed: Dec. 19, 2003

(65) Prior Publication Data

US 2004/0150428 A1    Aug. 5, 2004

(30) Foreign Application Priority Data

Dec. 26, 2002  (JP) .............................. 2002-376087
Apr. 24, 2003  (JP) .............................. 2003-120335
Apr. 24, 2003  (JP) .............................. 2003-120370

(51) Int. Cl.
  *G01N 11/16*  (2006.01)
(52) U.S. Cl. ..................................... 73/54.41
(58) Field of Classification Search ................ 73/54.41
See application file for complete search history.

(56) References Cited

U.S. PATENT DOCUMENTS

| 3,564,463 | A | * | 2/1971 | Beaver et al. ............... 333/191 |
| 4,721,874 | A | * | 1/1988 | Emmert ....................... 310/333 |
| 4,741,200 | A | * | 5/1988 | Hammerle .................. 73/54.25 |
| 4,862,384 | A | * | 8/1989 | Bujard et al. ................. 702/54 |
| 5,201,215 | A |   | 4/1993 | Granstaff et al. .......... 73/54.41 |
| 5,287,033 | A | * | 2/1994 | Morton ................... 310/316.01 |
| 6,260,408 | B1| * | 7/2001 | Vig et al. ................... 73/64.53 |
| 6,334,356 | B1| * | 1/2002 | Kita et al. .................. 73/54.01 |
| 6,494,079 | B1| * | 12/2002 | Matsiev et al. ............ 73/24.05 |

FOREIGN PATENT DOCUMENTS

| JP | 4-1554     | 1/1992 |
| JP | 2002-148295 | 5/2002 |
| JP | 2002-156368 | 5/2002 |

OTHER PUBLICATIONS

A. Zhou et al; "Impedance analysis for the investigation of the behaviors of piezoelectric quartz crystal in the liquid at harmonic resonance"; *Sensors and Actuators*; vol. B 67; 2000; pp. 68-75./ Discussed in the specification.

(Continued)

*Primary Examiner*—Hezron Williams
*Assistant Examiner*—John Fitzgerald
(74) *Attorney, Agent, or Firm*—Armstrong, Kratz, Quintos, Hanson & Brooks LLP

(57) ABSTRACT

A piezoelectric resonator is immersed in a liquid, an AC signal is applied, and a local maximum of the conductance is determined. A frequency change due to the viscosity effect is determined from two frequencies of three frequencies including a resonance frequency that is applied at that local maximum, and first and second half-value frequencies at which a half-value conductance of half that local maximum is given. The influence of the mass effect can be eliminated, so that an accurate measurement of the viscosity change is possible. Moreover, if the substance to be analyzed that is contained in the liquid adheres to a reaction film of the piezoelectric resonator, the mass of the piezoelectric resonator changes, and the second half-value frequency is measured. It is thus possible to derive only the influence of the mass effect, since the half-value frequencies are not influenced by the viscosity effect.

6 Claims, 4 Drawing Sheets

OTHER PUBLICATIONS

European Search Report dated Nov. 23, 2004.
Martin S J et al: "Characterization of a Quartz Crystal Microbalance With Simultaneous Mass and Liquid Loading" Analytical Chemistry, American Chemical Society. Columbus, US, vol. 63, No. 20, Oct. 15, 1991, pp. 2272-2281, XP000577312 ISSN: 0003-2700 *p. 2276-p. 2280.
Hauptmann P, Lucklum R, Hartmann J, Auge J and Adler B: "Using the Quartz Microbalance Principle for Sensing Mass Changes and Damping Properties" Sensors and Actuators A, vol. 37-38, Aug. 1, 1993, pp. 309-316, XP009039339 *p. 309-p. 311; figure 3.

Zhou A et al: "Impedance analysis for the investigation of the behaviors of piezoelectric quartz crystal in the liquid at harmonic resonance" Sensors and Actuators B, Elsevier Sequoia S.A., Lausanne, CH, vol. 67, No. 1-2, Aug. 10, 2000, p. 68-75, XP004213477 ISSN: 0925-4005 * the whole document.
Zhang C and Feng Guanping: "Contributions of Amplitude Measurement in QCM Sensors" IEEE Transactions on Ultrasonics, Ferroelectrics and Frequency Control, vol. 43, No. 5, Sep. 30, 1996, XP002304659 * the whole document.

* cited by examiner

ANALYSIS METHOD USING PIEZOELECTRIC RESONATOR

FIELD OF THE INVENTION

The present invention relates to technology for analyzing trace materials contained in liquids using a piezoelectric resonator, and in particular, to analysis technology in which such analysis is performed with high precision.

BACKGROUND OF THE INVENTION

The principle of QCM is used in methods for measuring the interaction between biological substances, such as DNA or proteins, and in measurements applying antigen-antibody reactions.

Conventional biosensors using QCM excite a piezoelectric element (quartz resonator or the like), which is a sensor, and continuously measure the resonance frequency, or continuously measure the frequency of the resonance point (the point where the impedance is lowest) using an impedance analyzer, and measure the amount of the substance adsorbed to the piezoelectric element surface by the frequency change.

The resonance frequency of the piezoelectric element (quartz resonator) immersed in the liquid fluctuates not only when the mass is changed, but also when the viscosity is changed. When the frequency fluctuation due to changes in mass is referred to as "mass effect," and the frequency fluctuation due to viscosity fluctuation is referred to as "viscosity effect," then, of the frequency fluctuations, the fluctuation amount due to the mass effect and the fluctuation amount due to the viscosity effect cannot be separated by the conventional approach of measuring only the fluctuations at the resonance frequency.

For example, when trying to examine the interaction between biological substances, such as DNA or proteins, by measuring frequency fluctuations, or when trying to examine antigen-antibody reactions by frequency fluctuations, then the viscosities of the sample injected into the measurement system and the employed buffer solution (biochemical buffer solution whose principal component are NaCl and KCl or the like) are different. As such, it becomes impossible to distinguish whether the measured frequency fluctuation value stems from the mass effect due to DNA and protein binding and antigen-antibody binding, or from the viscosity effect due to temperature changes or adding of sample substance, and thus an accurate measurement is impossible.

Regarding analysis technologies using piezoelectric resonators, the following related background art is known:
Patent Document 1: JPA 2002-148295
Patent Document 2: JPA 2002-156368
Patent Document 3: JPA H4-1554

The present invention has been made in order to solve the problems in the related art, and it is an object of the present invention to provide a technology for accurately determining mass changes of a piezoelectric resonator without being influenced by the viscosity effect.

SUMMARY OF THE INVENTION

First, the principle of an analysis method using a piezoelectric resonator as in the present application is explained. The following is an outline of the basic document (Anhong Zhou, et al., Impedance analysis for the investigation of the behaviors of piezoelectric quartz crystal in the liquid at harmonic resonance, Sensors and Actuators B 67 (2000) 68–75), which is the technology on which the present invention is based.

2.1 Derivation of Sauerbery Equation at Harmonic Resource

The oscillating frequency f of the crystal can be described by:

$$f = hf_0 = h\frac{1}{2t_Q}\left(\frac{\mu_Q}{\rho_Q}\right)^{1/2} \quad (1)$$

where h is the harmonic number (h=1, 3, 5 . . . ), $\mu_Q$ and $\rho_Q$ are the shear modulus and density of quartz, respectively $t_Q$ is the thickness of the crystal.

Considering the partial derivation of f in Eq. (1) with respect to $t_Q$ and the small change in the mass of the crystal surface (<1%)dm, dm=$P_Q$A$dt_Q$, the relationship between frequency change $\Delta f_m$ and the mass change $\Delta m$ can be simply derived.

$$\Delta f_m = -\frac{2Nhf_0^2}{(\rho_Q\mu_Q)^{1/2}}\frac{\Delta m}{A} \quad (2)$$

where A is the piezoelectrically active area of the electrode, N is the number of the sides in contact with the liquid.

It is obvious that when N=1 and h=1, Eq. (2) leads to the Sauerbrey equation [4]. Eq. (2) is assumed that the foreign film on electrode surface should be rigid and sufficiently thin [1.3].

Indeed, the frequency change of PQC in viscous liquids relates not only to the mass adlayer, but also to the physico-chemical properties [3], e.g. the density and viscosity of the liquid.

2.2 The Viscous Effect at Harmonic Resonance

The PQC can be electrically represented by the Butterworth-Van Dyke (BVD) equivalent circuit model [17, 18] as shown in FIG. 1. If the electrode area A and harmonic number h are considered, the impedance Z can be expressed as [19]:

$$Z_L = R_L + jX_L = NA(1+j)(\pi f_0 h \rho_L \eta_L)^{1/2} \quad (3)$$

where $$R_L = NA(\pi f_0 h \rho_L \eta_L)^{1/2} \quad (3a)$$

$$X_L = NA(\pi f_0 h \rho_L \eta_L)^{1/2} \quad (3b)$$

where the real part of Z is the resistance ($R_L$) and the imaginary part is the reactance ($X_L$), $\rho_L$ and $\eta_L$ are the absolute density and viscosity of the liquid, respectively.

When a crystal is in the ideally viscous liquid (Newtonian liquid), Mason ([20] stated that the (mechanical) shear impedance is also given by:

$$Z_L = \omega_L m_L + j\omega_L m_L \quad (4)$$

$m_L$ is the equivalent vibrating mass for viscous liquid loading on the crystal and can be obtained by combining Eqs. (3) and (4), $$m_L = A\left(\frac{\rho_L \eta_L}{4\pi f_0 h}\right)^{1/2} \quad (4a)$$

In this case, $m_L$ in Eq. (4a) is identified with m in Eq. (2). Substituting Eq. (4a) into Eq. (2) yields the frequency changes $\Delta f_L$ due to the liquid loading (considering the parameter N):

$$\Delta f_L = -\frac{Nh^{1/2}f_0^{3/2}(\rho_L\eta_L)^{1/2}}{(\pi\rho_Q\mu_Q)^{1/2}} \quad (5)$$

For N=1 and h=1, Eq.(5) agrees with the prediction of Kanazawa and Gordon [7] who derived from a model that couples the shear wave in the quartz to a damped stress wave in the liquid.

Eq.(5) indicates the viscous effect on the frequency response of PQC in the liquid phase. Therefore, the total frequency changes ($\Delta f$) due to the liquid loading plus mass effect is approximately obtained:

$$\Delta f = \Delta f_m + \Delta f_L \quad (6)$$
$$= -\frac{2Nhf_0^2}{(\rho_Q\mu_Q)^{1/2}}\frac{\Delta m}{A} - \frac{Nh^{1/2}f_0^{3/2}(\rho_L\eta_L)^{1/2}}{(\pi\rho_Q\mu_Q)^{1/2}}$$

This result is in accordance with that derived by Martin et al. [16], which is based on a continuum electromechanical model.

It should be emphasized that the frequency change monitored by oscillator method is confined to the total frequency change($\Delta f$), neither $\Delta f_m$, nor $\Delta f_L$.

3. The Relationship Between $\Delta f$ and $R_1$

In impedance analysis, Martin et al.'s model [16] can xeffectively characterize PQC with simultaneous mass and liquid loading. The motional resistance R2 for PQC under liquid loading can be expressed as [16]:

$$R_2 = \frac{N\omega L_1(2\omega\rho_L\eta_L)^{1/2}}{h\pi(\rho_Q\mu_Q)^{1/2}} \quad (7)$$

where $L_1$ represents the motional inductance in vacuum $$L_1 = \frac{1}{\omega^2 C_1} = \frac{(h\pi)^{1/2}}{\omega^2 8K_0^2 C_0} = \frac{1}{32f_0^2 K_0^2 C_0} \quad (8)$$

Substituting Eq.(8) into (7) yields:

$$R_2 = \frac{Nh^{1/2}\pi^{1/2}}{8f_0^{1/2}K_0^2 C_0}\left(\frac{\rho_L\eta_L}{\rho_Q\mu_Q}\right)^{1/2} \quad (9)$$
$$= 4Nh^{1/2}\pi^{1/2}f_0^{3/2}L_1\left(\frac{\rho_L\eta_L}{\rho_Q\mu_Q}\right)^{1/2}$$

where $K_0$ is a constant as defined in Ref. [16]: $K_0^2=e_{26}^2/(\bar{c}_{66}\epsilon_{22})$, $\bar{c}_{66}$ is the "piezoelectrically stiffened" quartz elastic constant, $e_{26}$ and $\epsilon 22$ are the piezoelectric stress constant and permittivity of the quartz, respectively.

For a crystal in a liquid, the notional resistance $R_1$ was divided into two parts in Martin's model, $R_1=R_q+R_2$, where $R_q$ is the motional resistance for an unperturbed PQC (i.e. PQC resonating in vacuum or in air). For instance, the $R_q$ measured in an air is ca. 15.0 $\Omega$ for a present 9 MHz crystal, compared with the measured R1, ca. 228 $\Omega$, for the same crystal in pure water (20° C.). In order to obtain a simple relationship of $\Delta f$ vs. $R_1$ when only mass and viscous effects are taken into account, it is reasonable to consider $R_1 \approx R_2$ in the present work. Therefore, the relationship of $\Delta f$ vs. $R_1$ can be approximately obtained by combining Eqs. (6) and (7), $$\Delta f = -\frac{2Nhf_0^2}{(\rho_Q\mu_Q)^{1/2}}\frac{\Delta m}{A} - \frac{1}{4\pi L_1}R_1 \quad (10)$$

Considering L1 in Eq(8), the slope of Eq. (10) is also described by:

$$-\frac{1}{4\pi L_1} = -\frac{8f_0^2 K_0^2 C_0}{\pi} \quad (10a)$$

This slope is only related to $f_0$, $K_0$ and $C_0$(or $L_1$), other than N and h. By measuring $L_1$ in vacuum (or in air), the theoretical value of this slope would be obtained.

The references are mentioned below.

[3]: D. A. Buttry, M. D. Ward, Measurement of interfacial processes at electrode surfaces with the electrochemical quartz crystal microbalance, Chem. Rev. 92 (1992) 1355–1379.

[4]: G. Sauerbrey, Verwendung von Schwingquarzen zur Wagung dunner Schichten und zur Mikrowagung, Z. Phys. 155(1959)206–222.

[7]: K. K. Kanazawa, J. G. Gordon II, The oscillation frequency of a quartz resonator in contact with a liquid, Anal. Chem. Acta 175 (1985)99–105.

[16]: S. J. Martin, V. E. Granstaff, G. C. Frye, Characterizaiton of a quartz microbalance with simultaneous mass and liquid loading, Anal. Chem. 63 (1991)2272–2281

[17]: W. G. Cady, Piezoelectricity, Dover, N.Y., 1964.

[18]: V. E. Bottom, in: Introduction to Crystal Unit Design, Van Nostrand-Reinhold, New York, 1982, p, 120.

[19]: W. P. Mason, Piezoelectric Crystals and Their Applications to Ultrasonics, Van Nostrand, Princeton, N.J., p. 339.

[20]: W. P. Mason, Electromechanical Transducers and Wave Filters, Van Nostrand-Reinhold, New York, 1948.

Considerations Regarding the Frequency

Next, when Y denotes the admittance, G denotes the conductance, B denotes the susceptance (admittance Y=conductance G+j susceptance B), and $\omega$ denotes the angular frequency, the conductance G and the susceptance B can be expressed by the following Equations (a) and (b), with the notional resistance $R_1$, the notional capacitance $C_1$, the motional inductance $L_1$ and the static capacitance $C_0$ of the equivalent circuit in FIG. 1.

$$G = \frac{R_1}{R_1^2 + \left(\omega L_1 - \frac{1}{\omega C_1}\right)^2} \quad (a)$$

-continued $$B = -\frac{\left(\omega L_1 - \frac{1}{\omega C_1}\right)}{R_1^2 + \left(\omega L_1 - \frac{1}{\omega C_1}\right)^2} + \omega C_0 \qquad (b)$$

When the angular frequency applied in the state of series resonance is taken to be the resonance angular frequency $\omega_s$, then $\omega_s L_1 - 1/(\omega_s C_1) = 0$ becomes true for the resonance angular frequency $\omega_s$ for h=1, so that the resonance angular frequency $\omega_s$ can be expressed by the following Equation (c):

$$\omega_s = \frac{1}{\sqrt{L_1 C_1}} \qquad (c)$$

Expressing the frequency corresponding to the angular frequency $\omega$ by f ($f=\omega/(2\pi)$), the resonance frequency $f_s$ can be expressed by the following Equation (d):

$$f_s = \frac{1}{2\pi\sqrt{L_1 C_1}} \qquad (d)$$

The conductance G for the resonant state of h=1 is $1/R_1$.

Here, the value of the conductance G for the resonant state is expressed by $G_s$, and taking half that value as the half-value conductance $G_s/2$ and taking the angular frequency at which the half-value conductance $G_s/2$ is given as the half-value angular frequency, there are two different half-value angular frequencies, namely a first half-value angular frequency $\omega_1$ that is lower than the resonance frequency $f_s$ and a second half-value angular frequency $\omega_2$ that is higher than the resonance frequency $f_s$ ($\omega_1 < \omega_2$).

The first and the second half-value frequencies $\omega_1$ and $\omega_2$ are given by the following Equations (e) and (f):

$$\omega_1 = \frac{1}{2} \cdot \frac{-R_1 C_1 + \sqrt{R_1^2 C_1^2 + 4L_1 C_1}}{L_1 C_1} \qquad (e)$$

$$\omega_2 = \frac{1}{2} \cdot \frac{R_1 C_1 + \sqrt{R_1^2 C_1^2 + 4L_1 C_1}}{L_1 C_1} \qquad (f)$$

FIG. 2 is a graph illustrating the relation between the resonance angular frequency $\omega_s$ for h=1, the first and second half-value angular frequencies $\omega_1$ and $\omega_2$ and the conductance G.

The first and second half-value frequencies $f_1$ and $f_2$ corresponding to the first and the second half-value angular frequencies $\omega_1$ and $\omega_2$ can be expressed by the following Equations ($g_1$) and ($g_2$):

$$f_1 = \frac{\omega_1}{2\pi} = \frac{1}{4\pi} \cdot \frac{-R_1 C_1 + \sqrt{R_1^2 C_1^2 + 4L_1 C_1}}{L_1 C_1} \qquad (g_1)$$

$$= \frac{R_1}{4\pi L_1} + \frac{\sqrt{R_1^2 C_1^2 + 4L_1 C_1}}{4\pi L_1 C_1}$$

$$f_2 = \frac{\omega_2}{2\pi} = \frac{1}{4\pi} \cdot \frac{R_1 C_1 + \sqrt{R_1^2 C_1^2 + 4L_1 C_1}}{L_1 C_1} \qquad (g_2)$$

$$= \frac{R_1}{4\pi L_1} + \frac{\sqrt{R_1^2 C_1^2 + 4L_1 C_1}}{4\pi L_1 C_1}$$

Mass Effect

First, the influence of mass changes, that is, the term for frequency changes due to the mass effect is explained.

In the second term of the above Equations ($g_1$) and ($g_2$), the value of $C_1$ is small, so that $R_1^2 C_1^2$ will take on a very small value and thus can be ignored. Consequently, Equations ($g_1$) and ($g_2$) can be rewritten as the following Equations ($h_1$) and ($h_2$):

$$f_1 = -\frac{R_1}{4\pi L_1} + \frac{\sqrt{4 L_1 C_1}}{4\pi L_1 C_1} \qquad (h_1)$$

$$f_2 = \frac{R_1}{4\pi L_1} + \frac{\sqrt{4 L_1 C_1}}{4\pi L_1 C_1} \qquad (h_2)$$

The second term of these Equations ($h_1$) and ($h_2$) is equivalent to the resonance frequency $f_s$, so that the first and the second half-value frequencies $f_1$ and $f_2$ can be expressed by the following Equations ($i_1$) and ($i_2$):

$$f_1 = -\frac{R_1}{4\pi L_1} + f_s \qquad (i_1)$$

$$f_2 = \frac{R_1}{4\pi L_1} + f_s \qquad (i_2)$$

If both the viscosity effect and the mass effect influence the equivalent circuit, and if it is assumed that the notional capacitance $C_1$ does not change whereas the notional inductance $L_1$ and the motional resistance $R_1$ do change, then $R_1$, $L_1$ and $f_s$ become $\Delta R_1$, $\Delta L_1$ and $\Delta f_s$, so that Equations ($i_1$) and ($i_2$) can be rewritten into ($i_{12}$) and ($i_{22}$).

$$\Delta f_1 = -\frac{\Delta R_1}{4\pi L_1} + \frac{R_1 \cdot \Delta L_1}{4\pi L_1^2} + \Delta f_s \qquad (i_{12})$$

$$\Delta f_2 = \frac{\Delta R_1}{4\pi L_1} - \frac{R_1 \cdot \Delta L_1}{4\pi L_1^2} + \Delta f_s \qquad (i_{22})$$

Here, if only $L_1$ changes in Equation (d), then $\Delta f_s$ becomes:

$$\Delta f_s = -\frac{1}{2\pi\sqrt{L_1 C_1}} \cdot \frac{\Delta L_1}{2 L_1} = -f_s \cdot \frac{\Delta L_1}{2 L_1}$$

$$\therefore \frac{\Delta f_s}{f_s} = -\frac{1}{2} \frac{\Delta L_1}{L_1}$$

so that when Equation ($i_{12}$) is rewritten using the above equation, then $\Delta f_1$ can be obtained with the following Equation ($i_{13}$) Similarly, by rewriting Equation (i22), $\Delta f_2$ can be obtained with the following Equation ($i_{23}$).

$$\Delta f_1 = -\frac{\Delta R_1}{4\pi L_1} + \Delta f_s\left(1 - \frac{R_1}{8\pi L_1 f_s}\right) \quad (i_{13})$$

$$\Delta f_2 = \frac{\Delta R_1}{4\pi L_1} + \Delta f_s\left(1 + \frac{R_1}{8\pi L_1 f_s}\right) \quad (i_{23})$$

In practice, for a quartz resonator with $f_s=27$ MHz, $R1\approx 200$ Ω, $L_1\approx 2\times 10^{-3}$ H are valid in a solution, so that $R_1/(8\pi L_1 f_s)$ in Equation ($i_{13}$) takes on the following value:

$$\frac{R_1}{8\pi L_1 f_s} = \frac{2\times 10^{-4}}{8\cdot 3\cdot 2\times 10^{-3}\cdot 2.7\times 10^7} = 1\times 10^{-4} \ll 1$$

This value is sufficiently smaller than 1, so that Equation ($i_{13}$) can be approximated to the following Equation ($j_1$). Similarly, Equation ($i_{22}$) can be approximated to the following Equation ($j_2$).

$$\Delta f_1 = -\frac{\Delta R_1}{4\pi L_1} + \Delta f_s \quad (j_1)$$

$$\Delta f_2 = \frac{\Delta R_1}{4\pi L_1} + \Delta f_s \quad (j_2)$$

Here, when considering only the mass effect and the viscosity effect, the frequency fluctuations $\Delta f$ can be expressed by the above Equation (10), so that infinitesimal changes $\Delta f_s$ of the resonance frequency $f_s$ can be expressed directly by the following Equation (k), using the above Equation (10):

$$\Delta f_s = -\frac{2hf_0^2}{(\rho_Q \mu_Q)^{1/2}} \frac{\Delta m}{A} - \frac{1}{4\pi L_1}\Delta R_1 \quad (k)$$

$\Delta f_s$ : Series resonant frequency change
$f_0$ : Fundamental frequency
$\rho_Q$ : Density of quartz $(2.648\ g/cm^2)$
$\mu_Q$ : Elastic constant of quartz piezoelectrically stiffened $(2.947\times 10^{11}\ g/cm\cdot S^2)$
$\Delta m$ : Mass change
$A$ : First and second eletrode area
$h$ : Harmonic number ($h = 1, 3, 5, \ldots$)
$L_1$ : Motional inductance
$\Delta R_1$ : Motional resistance change Substituting Equation (k) into Equations ($j_1$) and ($j_2$), small frequency changes $\Delta f_1$ and $\Delta f_2$ of the first and second half-value frequencies $f_1$ and $f_2$ can be expressed by the following Equations ($l_1$) and ($l_2$):

$$\Delta f_1 = -2\times \frac{\Delta R_1}{4\pi L_1} - \frac{2hf_0^2}{(\rho_Q \mu_Q)^{1/2}}\frac{\Delta m}{A} \quad (l_1)$$

$$\Delta f_2 = -\frac{2hf_0^2}{(\rho_Q \mu_Q)^{1/2}}\frac{\Delta m}{A} \quad (l_2)$$

From Equations ($l_1$) and ($l_2$) it follows that in Equation ($j_1$), the first term in Equation ($j_1$) is doubled, but in Equation ($j_2$) the first term is cancelled by the second term of Equation (k), and in Equation ($l_2$), the term including the infinitesimal change $\Delta R_1$ of the motional resistance $R_1$ is cancelled, and only the term with the infinitesimal change $\Delta m$ of the mass m as the variable remains. In other words, the term for the influence of the viscosity changes is cancelled, and the equation expresses the frequency change due to only the mass load.

Consequently, by measuring not the resonance frequency $f_s$, but the second half-value frequency $f_2$, it becomes possible to measure the frequency change due to only the mass load, excluding the influence of viscosity.

It should be noted that due to the mass change, also the value of the conductance G in the resonant state changes, so that when measuring the second half-value frequency $f_2$, the conductance $G_s$ of the resonant state is measured immediately before measuring the second half-value frequency $f_2$, and the half-value conductance $G_s/2$ is derived from this value, and the second half-value frequency $f_2$ can be determined from the greater frequency of the frequencies at which the half-value conductance $G_s/2$ is given.

Viscosity Effect

Next, the frequency changes excluding the mass effect, that is, the frequency changes due to the viscosity effect are determined.

The above Equation ($l_2$) expresses the frequency change due to the mass effect, and the above Equation (k) is the change in which the frequency change due to the mass effect and the frequency change due to the viscosity effect have been added, so that the frequency change due to the viscosity effect can be determined by subtracting Equation (l) from Equation (k).

In other words, when Equation ($l_2$) is subtracted from Equation (k) to determine $|\Delta f_s - \Delta f_2|$, the first term in Equation (k) is cancelled, and the frequency change $\Delta f_v$ due to the viscosity effect can be expressed by the following Equation (m).

$$\Delta f_v = |\Delta f_s - \Delta f_2| = \frac{\Delta R_1}{4\pi L_1} \quad (m)$$

Consequently, if the resonance frequency change $\Delta f_s$ and the frequency change $\Delta f_2$ of the second half-value frequency $f_2$ are measured, then the frequency change $\Delta f_v$ due to the viscosity effect can be determined from Equation (m), and hence the viscosity change of the solution can be determined.

Moreover, when $f_D$ is the frequency difference $|f_2-f_1|$ between the first and the second half-value frequencies $f_1$ and $f_2$, then this frequency difference $f_D$ can be determined directly from the Equations ($g_1$) and ($g_2$) and expressed by the following Equation (n):

$$f_D = |f_2 - f_1| = 2 \cdot \frac{R_1}{4\pi L_1} \tag{n}$$

Considering only the influence of the mass effect and the viscosity effect, the frequency change $\Delta f_D$ of the frequency difference $f_D$ can be expressed by the following Equation (o):

$$\Delta f_D = 2 \cdot \frac{\Delta R_1}{4\pi L_1} \tag{o}$$

From Equation (o) and Equation (m), the following Equation (p) is obtained:

$$\Delta f_D = 2 \cdot \Delta f_v \tag{p}$$

Consequently, if the first and second half-value frequencies $f_1$ and $f_2$ are consecutively measured, and the frequency change $\Delta f_D$ of the frequency difference $f_D$ is determined, then the frequency change $\Delta f_v$ of the resonance frequency $f_v$ due to the viscosity effect can be determined from the above Equation (p). Moreover, Equation (m) can be determined from Equations ($l_1$) and ($l_2$).

The above-described case is for h=1, and considering the conductance $G_s$ and the half-value conductance $G_s/2$ for the series resonance state at the fundamental resonance frequency, but also for an h of 2 or greater, the frequency change due to the viscosity effect can be similarly determined.

When the resonance frequency taking h into account is expressed as $f(h)_s$, the first and second half-value frequencies taking h into account are expressed as $f(h)_1$ and $f(h)_2$, and h is set to odd numbers (1, 3, 5, . . . ), then there is a resonance frequency $f(h)_s$ for each h, at which a series resonant state is attained, as shown in FIG. 3, and in the resonant state, the conductance takes on local maxima $G(h)_s$ (for h=1, the maximal value (local maxima) becomes the maximum value of the conductance G).

When the value used for h has been decided, the half-value conductance $G(h)_s/2$ which is the half value of the local maxima $G(h)_s$ of conductance corresponding to the value h, is obtained. The first and second half-value frequencies $f(h)_1$ and $f(h)_2$ are obtained by the half-value conductance $G(h)_s/2$.

Then, the frequency change $\Delta f(h)_v$ due to the viscosity effect under consideration of h can be determined from, among others, the frequency change $\Delta f(h)_s$ of the resonance frequency $f(h)_s$ and the frequency change $\Delta f(h)_D$ of the difference $f(h)_D$ between the first and second half-value frequencies $f(h)_1$ and $f(h)_2$.

Here, the relation between the frequency change $\Delta f(h)_v$ due to the viscosity effect and the density $\eta_1$ of the immersion liquid, as well as the relation to the frequency change $\Delta f(1)_v$ for the case that h=1 is expressed as in the following Equation (q):

$$\Delta f(h)_v = -h^{1/2} f_0^{3/2} (\rho_1 \eta_1 / \pi \rho_Q \mu_Q)^{1/2} \tag{q}$$
$$= h^{1/2} \cdot \Delta f(1)_v$$

-continued h : Harmonic number($h = 1, 3, 5, \ldots$)
$f_0$ : Fundamental frequency
$\rho_1$ : Density of liquid
$\eta_1$: Viscosity of liquid
$\rho_Q$ : Density of quartz (2.648 g/cm$^2$)
$\mu_Q$ : Elastic constant of quartz piezoelectrically stiffened (2.947 × 10$^{11}$ g/cm·$S^2$)

Similarly, the frequency change $\Delta f(h)_m$ due to the mass effect taking account of h depends on the electrode area A, the mass m of the piezoelectric resonator, and the frequency change $\Delta f(1)_m$ for the case that h=1, as shown in the following Equation (r):

$$\Delta f(h)_m = -h \cdot 2 f_0^2 \Delta m \Big/ A (\rho_Q \mu_Q)^{\frac{1}{2}} \tag{r}$$
$$= h \cdot \Delta f(1)_m$$

h : Harmonic number($h = 1, 3, 5 \ldots$)
$f_0$ : Fundamental frequnecy
$\rho_Q$ : Density of quartz(2.648g/cm$^2$)
$\mu_Q$ : Elastic constant of quartz piezoelectrically stiffened (2.947×10$^{11}$ g/cm·$S^2$)
$\Delta m$ : Mass change
A : First and second electrode area Consequently, it is possible to determine the frequency fluctuations due to the influence of the mass effect also for values of h other than 1, and to determine the mass changes of the piezoelectric resonator from that value.

The first embodiment of the present invention is an analysis method including immersing a piezoelectric resonator having a crystal plate and first and second electrodes formed on the two sides of the crystal plate in a liquid, applying an AC signal to the first and second electrodes, and determining a mass change of the piezoelectric resonator from a relation between a frequency of the AC signal and an electric property of the piezoelectric resonator, wherein a first and second half value frequencies are frequency which give a half-value conductance and the half-value conductance is a half of conductance under series resonance state of the piezoelectric resonator, wherein the mass change of the piezoelectric resonator is determined by the change of the second half-value frequency which is close to the resonance frequency giving the series resonance state, and larger than the resonance frequency.

Furthermore, the first embodiment of the present invention is the analysis method, wherein an AC signal of a frequency range that is anticipated to include the second half-value frequency is consecutively input to the piezoelectric resonator, and the mass change of the piezoelectric resonator over time is determined.

The first embodiment of the present invention is the analysis method, wherein an initial value of the second half-value frequency is determined before the sample is given into the liquid, and the mass change of the piezoelectric resonator is determined from the fluctuation amount with respect to this initial value of the second half-value frequency.

The first embodiment of the present invention is the analysis method, wherein an extremum value of the conductance of the piezoelectric resonator is measured, and the second half-value frequency is determined from the extremum.

The first embodiment of the present invention is the analysis method, wherein the extremum value is a maximum value of the conductance of the piezoelectric resonator.

The first embodiment of the present invention is the analysis method, wherein the second half-value frequency is determined from the resonance frequency of the piezoelectric resonator and a constant of an equivalent circuit of the piezoelectric resonator.

The second embodiment of the present invention is an analysis method comprising, Immersing an excitable piezoelectric resonator in a liquid, and Applying an AC signal to the piezoelectric resonator, wherein a viscosity change of the liquid is determined from at least two frequencies of three frequencies including a resonance frequency that puts the piezoelectric resonator into a series resonance state, and first and second half-value frequencies obtaining a half-value conductance which is half conductance under the series resonance state of the piezoelectric resonator.

The second embodiment of the present invention is the analysis method, wherein the AC signal is repeatedly input to the piezoelectric resonator at a frequency range that is anticipated to include the resonance frequency, a frequency change of the difference of the two frequencies is determined over time, and the viscosity change is determined from the frequency change of the difference of the two frequencies.

The second embodiment of the present invention is the analysis method, wherein the piezoelectric resonator has a crystal plate and first and second electrodes formed on the two sides of the crystal plate and the AC signal is applied between the first and the second electrode.

The second embodiment of the present invention is the analysis method, wherein a frequency change due to influence of a mass change of the piezoelectric resonator is determined using the second half-value frequency, which is the greater one of the first and second half-value frequencies.

The second embodiment of the present invention is the analysis method, wherein a relation between conductance of the piezoelectric resonator and frequency is measured, and at least two of the three frequencies are determined.

Furthermore, the second embodiment of the present invention is the analysis method, wherein the maximum of the conductance is used.

The present invention is the analysis method, wherein the resonance frequency of the piezoelectric resonator and a constant of its equivalent circuit are used.

DESCRIPTION OF THE PREFERRED EMBODIMENTS

Apparatus

First, a piezoelectric resonator and a measurement apparatus that can be used for the present invention are explained.

Figure 1:
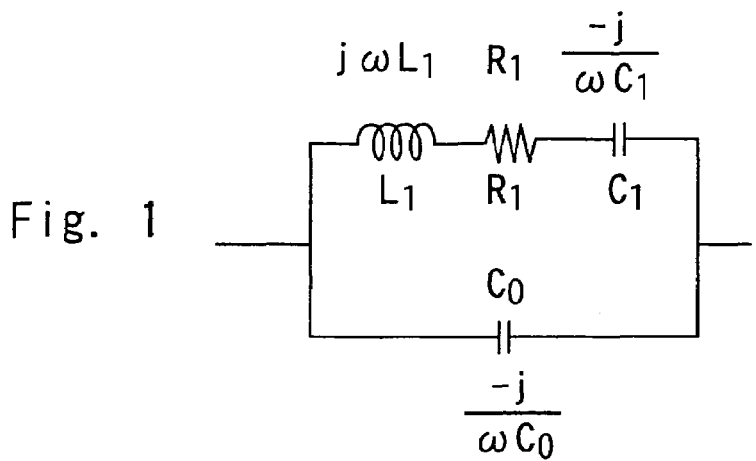
FIG. 1 shows an equivalent circuit of a piezoelectric resonator.
Figure 2:
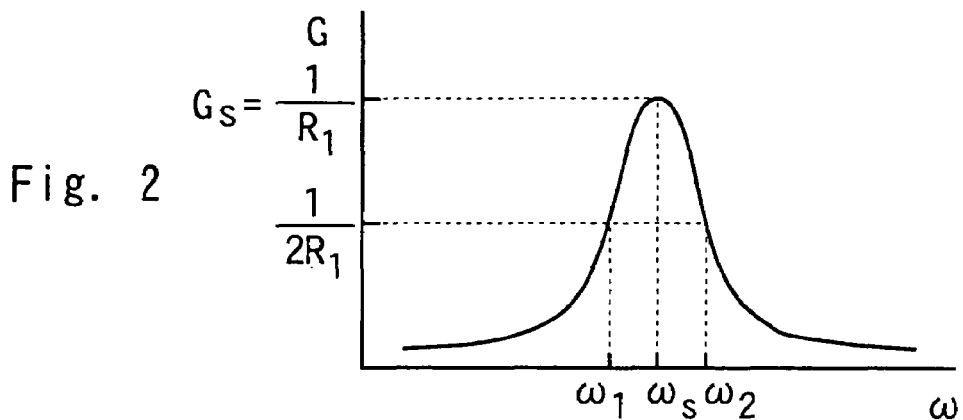
FIG. 2 is a graph showing the relation between a signal frequency and the conductance of the piezoelectric resonator.
Figure 3:
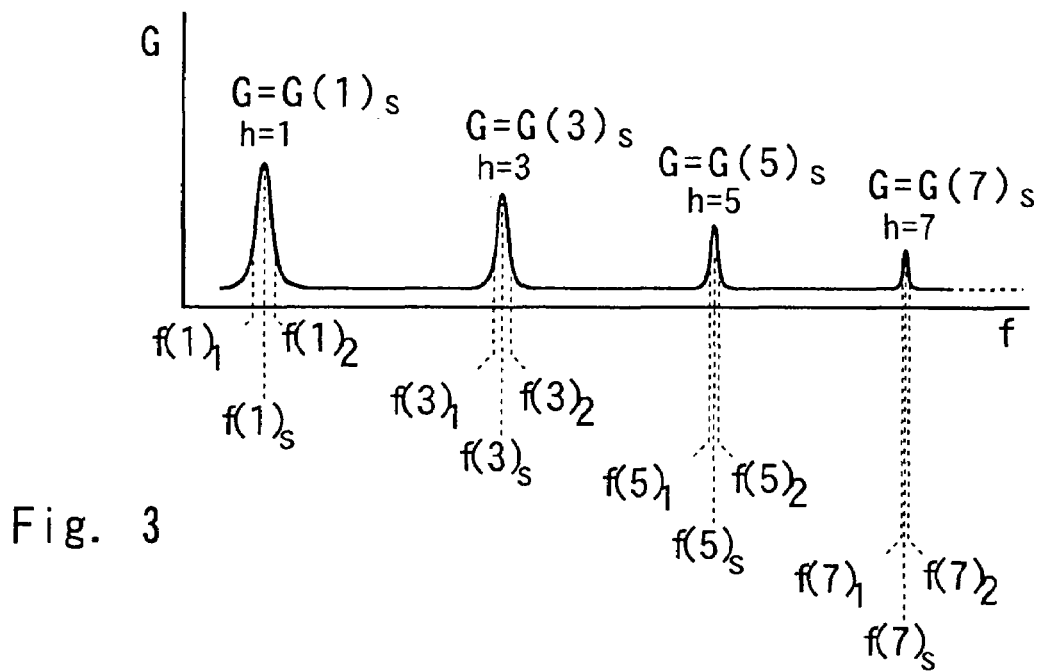
FIG. 3 is a graph illustrating the resonance states of the first and higher-order harmonics.
Figure 4A:
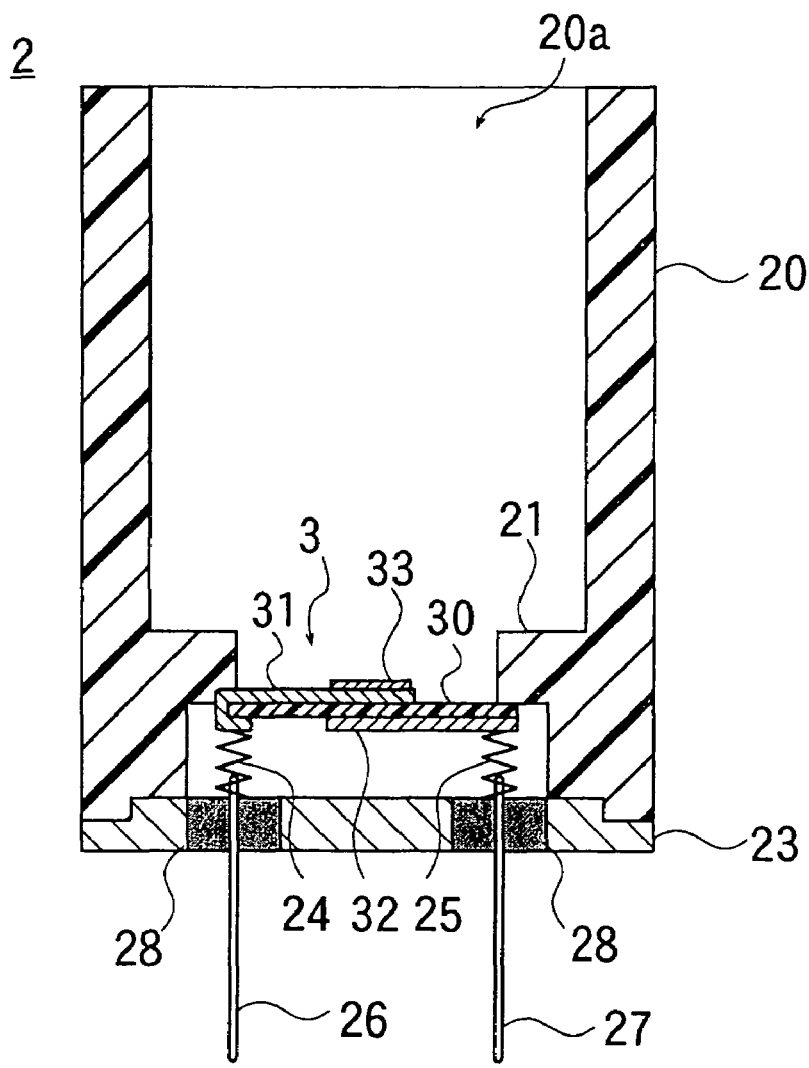
FIGS. 4A to 4C are diagrams illustrating a piezoelectric resonator according to the present invention and a measurement cell using that piezoelectric resonator.
Figure 4B:
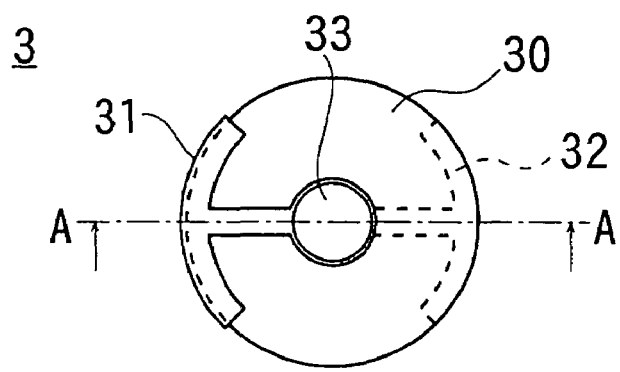

FIG. 4A is a cross-sectional view of a measurement cell 2 of an embodiment of the present invention; FIG. 4B is a plan view of a quartz resonator 3 of this measurement cell; and FIG. 4C is a cross-sectional view thereof.

Figure 4C:
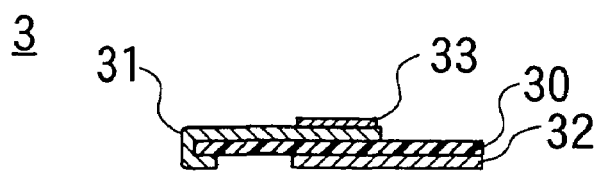

As shown in FIGS. 4B and 4C, the piezoelectric resonator 3 has a crystal plate 30, and a first and a second electrode 31 and 32 are arranged on the top surface and the rear surface side of this crystal plate 30, respectively. The crystal plate 30 is made by forming a crystal, such as a quartz crystal for example, into disk shape, and the first and second electrodes 31 and 32 are made by patterning metal films into a predetermined shape. A part of the first electrode 31 is wrapped around to the rear side of the crystal plate 30.

The first and second electrodes 31 and 32 are connected to ends of first and second springs 24 and 25 at the locations on the rear surface of the crystal plate 30. The other ends of the first and second springs 24 and 25 are connected to first and second terminal pins 26 and 27. The first and second springs 24 and 25 are made of metal, and the first and second electrodes 31 and 32 are electrically connected to the first and second terminal pins 26 and 27 via the first and second springs 24 and 25.

Reference numeral 23 denotes an insulating base, and the first and second connection pins 26 and 27 are fixed to this base 23 by glass seals 28.

As shown in FIG. 4A, the cell 2 has a cell body 20 made by, for example, acrylic resin formed into a tubular shape.

At a location slightly above the bottom of the cell body 20, a flange portion 21 is formed. The piezoelectric resonator 3 is inserted into the cell body 20 from the bottom side of the cell body 20, and the outer peripheral portion of the piezoelectric resonator 3 is in contact with the flange portion 21.

In this state, the first and second springs 24 and 25 are compressed, and the piezoelectric resonator 3 is pressed against the flange 21 by their restoring force.

An adhesive is arranged at the portion where the piezoelectric resonator 3 and the flange portion 21 are in contact, and while the outer periphery of the piezoelectric resonator 3 is pressed against the flange portion 21 by the first and second springs 24 and 25; the base 23 is fixed to the bottom face of the cell body 20; and the piezoelectric resonator 3 is fixed to the flange portion 21 by the adhesive.

In this state, a fluid-tight container portion 20a that is shaped like a tubular vessel with a bottom is constituted with the piezoelectric resonator 3 as a bottom surface, and the cell body 20 as the upper portion.

The first and second terminal pins 26 and 27 are drawn out of the cell body 20 from the bottom surface of the base 23, and by connecting the first and second terminal pins 26 and 27 to an external circuit of the measurement equipment or the like, the first and second electrodes 31 and 32 are connected to this external circuit.

Of the first and second electrodes 31 and 32, the first electrode 31 is arranged on the top surface side of the crystal plate 30, that is, at a location where it is exposed at the bottom surface of the container portion 20a, and a reaction film 33 is disposed on the surface of this first electrode 31. This reaction film 33 is made of a material that reacts with a specific component to be measured, or adsorbs this specific component.

Figure 5:
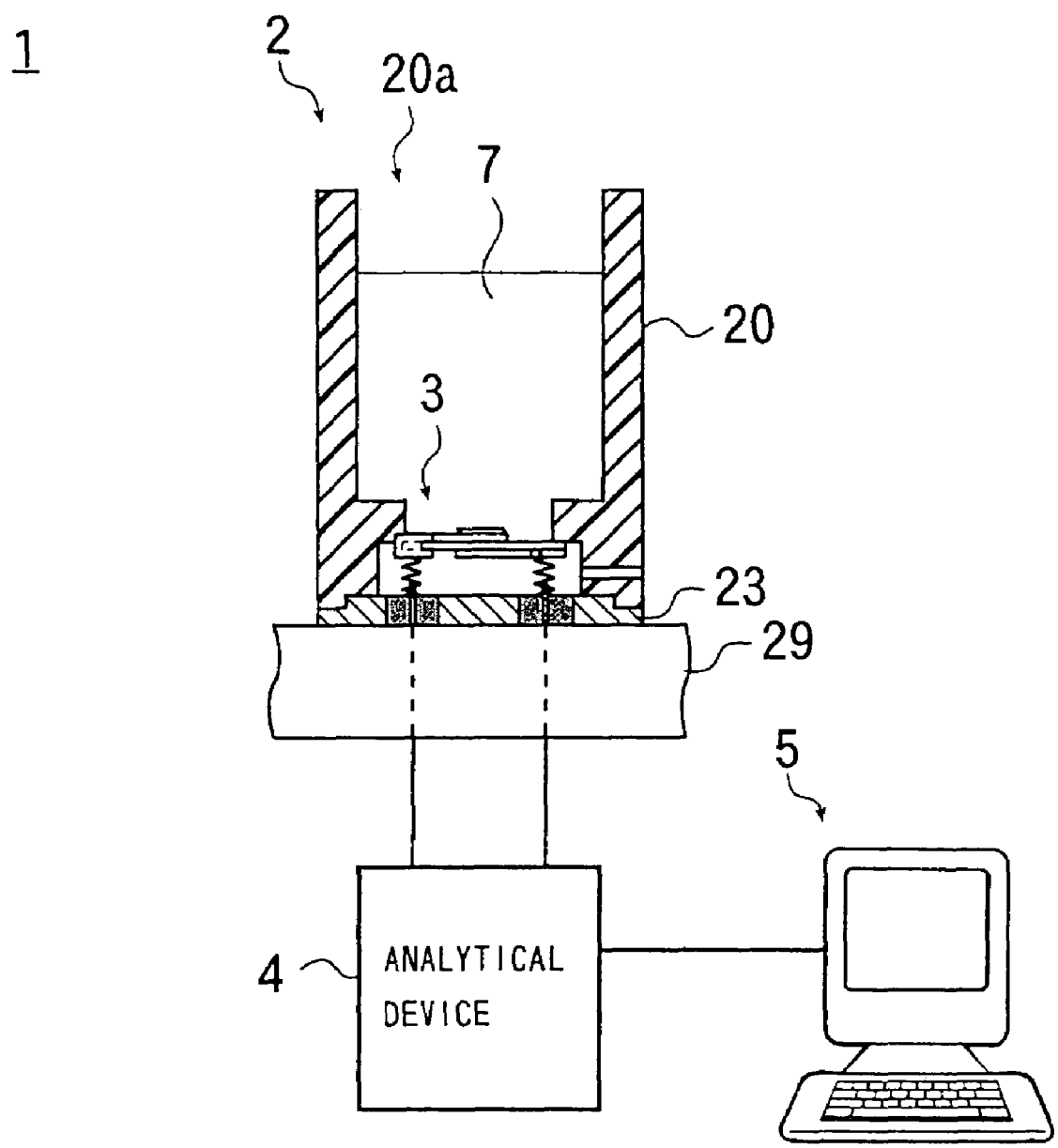
FIG. 5 is a diagram illustrating an entire measurement apparatus.

As shown in FIG. 5, the cell 2 is arranged on a platform 29, and a liquid, which is a solvent in which the specific component to be measured is dissolved, or a liquid in which the specific component is dispersed, but which does not yet contain the specific component, is filled into the container portion 20a.

Reference numeral 7 in FIG. 5 denotes this liquid, and in this state, the reaction film 33 is in contact with the liquid 7. The second electrode 32 positioned on the opposite site of the first electrode 31 is not in contact with the liquid 7. Consequently, in this example, N in the above Equations (1) to (10) is 1.

Reference numeral 1 in FIG. 5 denotes the measurement apparatus, which includes the above-mentioned cell 2, an analytical device 4 having such as a network analyzer or an impedance analyzer, and a control device 5 that controls the analytical device 4 and calculates the measurement value.

The cell 2 is connected to the analytical device 4, which outputs alternating current signal of the desired frequency to the cell 2, and the conductance G of the cell 2 at this frequency can be measured.

Here, the control device 5 controls the operation of the analytical device 4, and the analytical device 4 changes the frequency of the signal that is output to the cell 2, correlates the frequency with the measurement result, and stores them together with the calculation result.

FIRST EXAMPLE

The following is a description of a first example of the present invention.

Using the above-described apparatus, the frequency is changed within a predetermined range including the resonance frequency $f_s$, and if the relation between the frequency and the conductance G is measured, then the conductance G takes on an extremum at the resonance frequency. In particular, the extremum value of the conductance G is a maximum in the resonance state of h=1, so that it can be easily seen that the frequency at which the maximum conductance $G_{max}$ during the measurement is the resonance frequency $f_s$. The measurement value of the resonance frequency $f_s$ before adding the sample is the initial value of the resonance frequency $f_s$.

Moreover, for h=1, the second half-value frequency $f_2$ can be determined from the measurement results as the frequency that is larger than the resonance frequency $f_s$ and at which the value of ½ of the maximum conductance $G_{max}$, that is, the half-value conductance $G_s/2$, is given. Before adding the sample, this value is the initial value $f_{M2}$ (t=0) of the second half-value frequency $f_2$.

Next, when giving, as the sample, a liquid including the specific component to be measured to the liquid 7, the specific compound reacts with or is adsorbed to the reaction film 33, and the weight of the reaction film 33 starts to increase.

Here, after adding the sample, a signal is applied to the cell 2 whose frequency is varied over a predetermined range that includes the initial value of the resonance frequency $f_s$ and the initial value of the second half-value frequency $f_2$, and then, the conductance G of the cell 2 is measured.

For example, if the second half-value frequency $f_2$ is determined every second, then the maximum value of the conductance G is measured in intervals of one second while changing the frequency of the AC signal at the predetermined range.

Moreover, from the measured values of the conductance G, the extremum is determined (for h=1, this is the maximum conductance $G_{max}$). The second half-value frequency $f_2$ is obtained by the half-value conductance which is ½ of conductance. After adding the sample, this procedure is repeated in constant intervals (for example, every second).

Here, when the measured values of the second half-value frequency $f_2$ are $f_{M2}(t=1)$, $f_{M2}(t=2)$, ... (t denotes time), then the mass fluctuation can be determined from the frequency difference between the measured values $f_{M2}(t=1)$, $f_{M2}(t=2)$, ... and the initial value $f_{M2}(t=0)$. Thus, from the mass fluctuation, the concentration of the specific component in the liquid to be measured can be determined.

It should be noted that it is also possible to record the measurement results every second, and to determine the second half-value frequency $f_2$ and its fluctuation after the measurement.

The following is an explanation about the high precision of the present invention, using a graph with actual measurement results.

Figure 6:
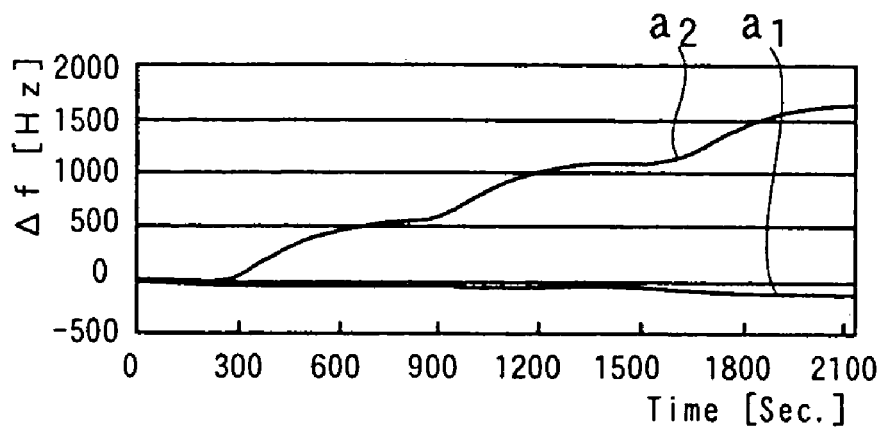
FIG. 6 is a graph illustrating the relation between temperature changes and frequency fluctuations.

Let $\Delta f$ be the frequency difference between the measured value of the second half-value frequency $f_2$ or measured value of the resonance frequency $f_s$ and the initial value. FIG. 6 is a graph showing the frequency difference $\Delta f$ and a time for the case that the piezoelectric resonator is immersed in water, and the water temperature is increased in steps of 5° from 20° C. to 35° C. In FIG. 6, $a_1$ denotes a curve showing the change of the frequency difference $\Delta f$ of the second half-value frequency $f_2$, and $a_2$ denotes a curve showing the change of the frequency difference $\Delta f$ of the resonance frequency $f_s$.

As the temperature is increased, the viscosity of the liquid decreases, so that the change in the frequency difference $\Delta f$ of the resonance frequency $f_s$ is large. On the other hand, the change of the frequency difference $\Delta f$ of the second half-value frequency $f_2$ is zero (the slight change that can be seen is due to variations of the properties of the quartz resonator as the temperature is changed).

Figure 7:
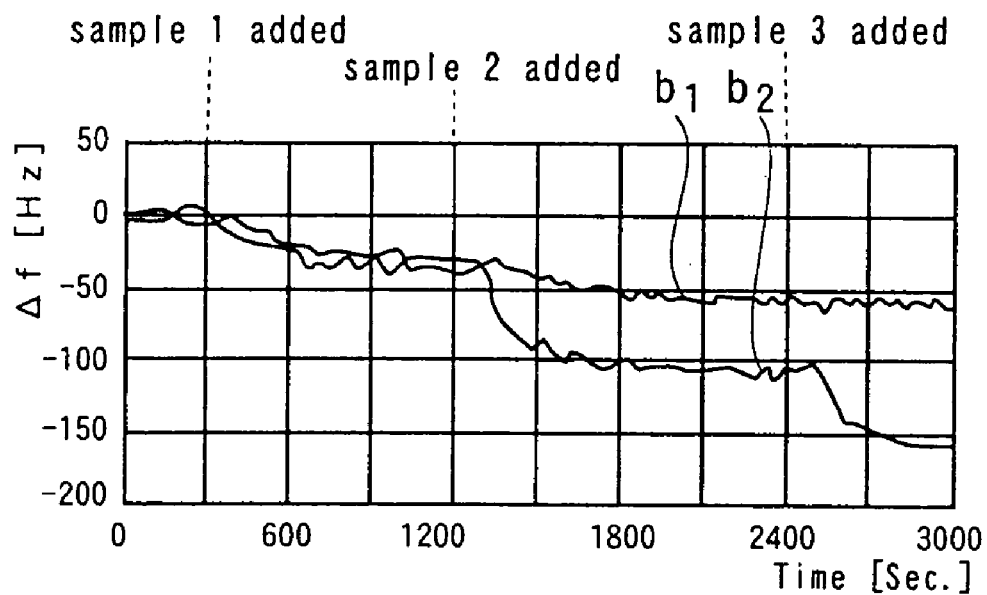
FIG. 7 is a graph illustrating the relation between mass effect and viscosity effect on the one hand and frequency fluctuations on the other hand.

FIG. 7 is a graph showing the changes over time of the frequency difference $\Delta f$ in the presence of both the mass effect and the viscosity effect. In FIG. 7, $b_1$ indicates the fluctuations of the frequency difference $\Delta f$ of the second half-value frequency $f_2$, and $b_2$ indicates the fluctuations of the frequency difference $\Delta f$ of the resonance frequency $f_s$.

In this graph, first, the time at which the piezoelectric resonator 3 was immersed in the buffer solution is taken as the measurement start time, and a first sample (avidin) was added at a time of 300 seconds after the measurement start time, then a second sample (liquid mixture of glycerol and avidin (with the same concentration of avidin as in the first sample)) was added at a time of 1200 seconds after the measurement start time, and after 2400 seconds had passed, a third sample (only glycerol, same amount as for the second sample) was added.

In these samples, avidin adheres to the reaction film 33 and imparts the mass effect, but glycerol does not adhere to the reaction film 33 and imparts only the viscosity effect.

By adding the first sample, the frequency differences $\Delta f$ change due to the adherence of avidin, but it changes with a constant slope for the second half-value difference $f_2$, whereas for the frequency difference $\Delta f$ of the resonance frequency $f_s$, the frequency is decreased greatly by the viscosity effect due to the glycerol.

In this example, it should be noted that the conductance G for the series resonance state is measured, and the second half-value frequency $f_2$ is determined from ½ that value. It is also possible not to measure the conductance G for the series resonance state and to calculate the second half-value resonance $f_2$ using the measured value of the resonance frequency $f_s$ and the constants $R_1$, $L_1$ and $C_1$ of the equivalent circuit.

For example, if the resistance $R_1$, the inductance $L_1$ and the resonance frequency $f_2$ of the oscillator 3 are measured, then the second half-value frequency $f_2$ can be calculated from Equation ($i_1$) without measuring the conductance G.

Moreover, if the Q value ($Q=f_s/(f_2-f_1)$) or the D value ($D=1/Q$) are measured with an impedance analyzer or the like, then the second half-value frequency $f_2$ can be determined from $f_2=f_s+f_s/(2 \cdot Q)$.

That is to say, the present invention is not limited to actually measuring the conductance G to determine the second half-value frequency $f_2$, but also includes the case that values other than the conductance G are measured to obtain the second half-value frequency $f_2$.

With the conventional approach, when the viscosities of the buffer solution and the sample differ, an accurate measurement is not possible, but the present invention is not susceptible to the modification effect by the Temperature change or using a sample whose viscosity is different from that of the buffer solution, so that an accurate measurement becomes possible.

Consequently, the present invention is very effective for the testing of, for example, blood, which has high viscosity, or for testing for germs in food.

Moreover, since it is not affected by temperature, after putting the cell filled with buffer solution in the apparatus, the stabilization time until the temperature of the buffer has reached the temperature set with the apparatus can be shortened, thus increasing the throughput.

Furthermore, substances that include a lot of water resonate together with water when adhered, so that there were frequency vibrations larger than the true value with the conventional technology, but the correct measurement can be performed with the present invention.

SECOND EXAMPLE

The following is a description of a second example of the present invention.

In this example, a frequency range including the resonance frequency $f_s$ of the cell 2, and the first and second half-value frequencies $f_1$ and $f_2$ is set beforehand, the frequency is changed within this range. The value of the conductance G is measured, and the frequency f applied to the cell 2 and the value of the conductance G at that frequency f are stored in correlation.

If there is only one resonance state within the frequency range used for the measurement, then the frequency f at which the maximum value $G_{max}$ of the conductance G is given within that frequency range will be the resonance frequency $f_s$.

Moreover, from the relation between the stored frequency f and the conductance G, the first and second half-value frequencies $f_1$ and $f_2$ at which ½ of the maximum value $G_{max}$ of the conductance G (that is, the half-value conductance $G_s/2$) is given are determined.

The measured values of resonance frequency $f_s$ and the first and second half-value frequencies $f_1$ and $f_2$ before adding the sample are the initial values.

Next, when giving a liquid including the specific component to be measured as the sample to the liquid 7, the specific compound reacts with or is adsorbed to the reaction film 33, and the weight of the reaction film 33 increases, and as the reaction proceeds, the viscosity changes.

After adding the sample, a signal whose frequency range is anticipated to include the resonance frequency $f_s$ and the first and second half-value frequencies is applied to the cell 2, and similar to when determining the initial value, the maximum value $G_{max}$ of the conductance G is determined, and the first and second half-value frequencies $f_1$ and $f_2$ are determined from the half-value conductance $G_s/2$.

Repeating this procedure at constant intervals (for example once every second) after adding the sample, the value obtained by subtracting the initial value from the measured value of the frequency after adding the sample is the frequency change at each measurement time. Consequently, utilizing the frequency change $\Delta f_s$ of the resonance frequency $f_s$ and the frequency change $\Delta f_2$ of the second half-value frequency $f_2$, the frequency change $\Delta f_v$ due to the viscosity effect can be determined from Equation (m), or utilizing the frequency changes $\Delta f_1$ and $\Delta f_2$ of the first and second half-value frequencies $f_1$ and $f_2$, the frequency change $\Delta f_v$ due to the viscosity effect can be determined from Equation (p).

Moreover, the frequency change due to the mass effect can be determined from the frequency change $\Delta f_2$ of the second half-value frequency $f_2$. From the frequency change due to the mass effect, the concentration of the specific component in the liquid to be measured can be known.

It should be noted that it is also possible to determine the frequency changes $\Delta f_s$, $\Delta f_1$ and $\Delta f_2$ at each measurement, or to record the measurement results and determine them in one step after the measurement has been finished.

In the foregoing description, the cell 2 had a reaction film 33 and the specific component to be measured in the sample was reacted or adsorbed to the reaction film 33, but if it is not necessary to determine the frequency changes due to the mass effect (for example, if the viscosity changes of the liquid for temperature fluctuations are determined), then the reaction film 33 of the cell 2 is not necessary; and it is possible to use a cell without a reaction film.

Moreover, in the above example, the relation between the conductance G and the frequency f was measured for the series resonance state, and the first and second half-value frequencies $f_1$ and $f_2$ were determined from the value of the half-value conductance $G_s/2$, which is ½ the maximum value $G_{max}$, but it is also possible to calculate the first and second half-value frequencies $f_1$ and $f_2$ using the measured value of the resonance frequency $f_s$ and the constants $R_1$, $L_1$ and $C_1$ of the equivalent circuit, without measuring the conductance G in the series resonance state.

For example, if the resistance $R_1$, the inductance $L_1$ and the resonance frequency $f_s$ of the piezoelectric resonator 3 are measured, then the first and second half-value frequencies $f_1$ and $f_2$ can be calculated from Equations (i) without measuring the conductance G. Therefore, it is possible to determine the frequency change $\Delta f_v$ due to the viscosity effect without measuring the conductance G.

Moreover, if the Q value ($Q=f_s/(f_2-f_1)$) or the D value ($D=1/Q$) are measured with an impedance analyzer or the like, then the frequency changes $\Delta f_v$ due to the viscosity effect can be determined from the resonance frequency $f_v$ and the Q value (or the D value).

In other words, the present invention is not limited to actually measuring the conductance G to determine the resonance frequency $f_s$ or the first or second half-value frequency $f_1$ or $f_2$.

Moreover, in the above example, the frequency changes $\Delta f_v$ due to the viscosity effect were determined based on Equation (m) or Equation (n) from a combination of the first half-value frequency $f_1$ and the resonance frequency $f_v$ or a combination of the first and second half-value frequencies $f_1$ and $f_2$, but the first term in Equation (k) and the second term in Equation ($l_1$) can be cancelled, so that it is possible to determine the frequency changes $\Delta f_v$ due to the viscosity effect also by combining the resonance frequency $f_s$ and the first half-value frequency $f_1$.

That is, it is possible to determine the frequency changes $\Delta f_v$ due to the viscosity effect using any two frequencies of the three frequencies including the resonance frequency $f_s$ and the first and second half-value frequencies $f_1$ and $f_2$.

As explained above, with the present invention, it is easy to determine the viscosity changes of samples.

Moreover, for the same samples, the frequency changes due to the mass effect and the frequency changes due to the viscosity effect can be determined together, so that detailed analysis of the sample becomes possible. Consequently, the present invention is very effective for testing, for example, blood, which has high viscosity, or for testing for germs in food.

What is claimed is:

1. An analysis method, comprising the steps of:
    immersing a piezoelectric resonator having a crystal plate and first and second electrodes formed on two sides of the crystal plate in a liquid;
    applying an AC signal to the first and second electrodes;
    determining a mass change of the piezoelectric resonator from a relation between a frequency of the AC signal and an electric property of the piezoelectric resonator;
    determining a half-value frequency which gives a half of conductance under a series resonance state of the piezoelectric resonator, and which is larger than a resonance frequency giving the series resonance state; and
    determining the mass change of the piezoelectric resonator by the change of the determined half-value frequency.

2. The analysis method according to claim 1,
    wherein the AC signal has a predetermined frequency range, the predetermined frequency range including the half-value frequency and being consecutively input to the piezoelectric resonator, and wherein the mass change of the piezoelectric resonator over time is determined.

3. The analysis method according to claim 1,
    wherein an initial value of the half-value frequency is determined before a sample is given into the liquid, and the mass change of the piezoelectric resonator is determined from the fluctuation amount with respect to this initial value of the half-value frequency.

4. The analysis method according to claim 1,
    wherein the half-value frequency is determined from the resonance frequency of the piezoelectric resonator and a constant of an equivalent circuit of the piezoelectric resonator.

5. The analysis method according to claim 1,
    wherein an extremum value of the conductance of the piezoelectric resonator is measured, and the half-value frequency is determined from the extremum.

6. The analysis method according to claim 5,
    wherein the extremum value is a maximum value of the conductance of the piezoelectric resonator.

* * * * *

UNITED STATES PATENT AND TRADEMARK OFFICE
CERTIFICATE OF CORRECTION

PATENT NO. : 7,111,500 B2
APPLICATION NO. : 10/739397
DATED : September 26, 2006
INVENTOR(S) : Itoh et al.

It is certified that error appears in the above-identified patent and that said Letters Patent is hereby corrected as shown below:

<u>In Column 7;</u>
on lines 5 through 10 change

"
$$\Delta f_1 = -\frac{\Delta R_1}{4\pi L_1} + \Delta f_s (1 - \frac{R_1}{8\pi L_1 f_s}) \cdots\cdots (i_{13})$$
$$\Delta f_2 = \frac{\Delta R_1}{4\pi L_1} + \Delta f_s (1 + \frac{R_1}{8\pi L_1 f_s}) \cdots\cdots (i_{23})$$
"

to be

--
$$\Delta f_1 = -\frac{\Delta R_1}{4\pi L_1} + \Delta f_s (1 - \frac{R_1}{2\pi L_1 f_s}) \cdots\cdots (i_{13})$$
$$\Delta f_2 = \frac{\Delta R_1}{4\pi L_1} + \Delta f_s (1 + \frac{R_1}{2\pi L_1 f_s}) \cdots\cdots (i_{23})$$
--

<u>In Column 7;</u>
on line 13 change "$R_1/(8\pi L_1 f_s)$" to be -- $R_1/(2\pi L_1 f_s)$ -- also on line 15 through 20 change

"
$$\frac{R_1}{8\pi L_1 f_s} = \frac{2 \times 10^{-4}}{8 \cdot 3 \cdot 2 \times 10^{-3} \cdot 2.7 \times 10^7} = 1 \times 10^{-4} \ll 1$$
"

UNITED STATES PATENT AND TRADEMARK OFFICE
CERTIFICATE OF CORRECTION

PATENT NO. : 7,111,500 B2
APPLICATION NO. : 10/739397
DATED : September 26, 2006
INVENTOR(S) : Itoh et al.

It is certified that error appears in the above-identified patent and that said Letters Patent is hereby corrected as shown below:

In Column 7 (cont'd);

to be

-- $$\frac{R_1}{2\pi L_1 f_s} = \frac{2 \times 10^2}{2 \cdot 3 \cdot 2 \times 10^{-3} \cdot 2.7 \times 10^7} = 0.6 \times 10^{-3} \ll 1$$ --

Signed and Sealed this

Seventh Day of August, 2007

JON W. DUDAS
*Director of the United States Patent and Trademark Office*